United States Patent [19]

Feng

[11] Patent Number: 5,357,976

[45] Date of Patent: Oct. 25, 1994

[54] METHOD OF AND ARRANGEMENT FOR DIAGNOSING BRAIN DISEASE

[75] Inventor: Genquan Feng, 34 Monroe St. Building C, #J-9, New York, N.Y. 10002-0016

[73] Assignee: Genquan Feng, New York, N.Y.

[21] Appl. No.: 994,492

[22] Filed: Dec. 21, 1992

Related U.S. Application Data

[60] Division of Ser. No. 822,525, Jan. 17, 1992, which is a continuation-in-part of Ser. No. 397,695, Oct. 30, 1989, abandoned.

[51] Int. Cl.$^5$ .......................................... A61B 5/0476
[52] U.S. Cl. .................................................. 128/731
[58] Field of Search .......................................... 128/731

[56] References Cited

U.S. PATENT DOCUMENTS

| | | | |
|---|---|---|---|
| 4,201,224 | 5/1980 | John | 128/731 |
| 4,545,388 | 10/1985 | John | 128/731 |
| 4,815,474 | 3/1989 | Duffy | 128/731 |
| 4,832,480 | 5/1989 | Kornacker et al. | 128/731 |
| 4,907,597 | 3/1990 | Chamoun | 128/731 |
| 5,083,571 | 1/1992 | Prichep | 128/731 |

*Primary Examiner*—William E. Kamm

[57] ABSTRACT

Brain disease is non-invasively, accurately diagnosed at an early stage. A plurality of functions descriptive of the patient are mathematically determined. A set of indices for each function is established in advance. Each index has two states indicative of the patient's condition. An integrated pattern of the states of the indices from a plurality of the functions is generated and matched against a stored collection of index patterns whose diagnosis is known.

16 Claims, 18 Drawing Sheets

POWER SPECTRUM OF THE BROAD AREA OF THE HEART

AMPLITUDE HISTOGRAM OF THE SIGNALS
OF BROAD AREA OF THE HEART

CROSS CORRELATION

```
84 ⎰   ***** CARDIOGRAM      ANALYSIS *****.
   ⎱   No. F8      NAME CHEN     SEX M    AGE 71    DATE
   ─────────────────────────────────────────────────────

⎧  1. P0
   ⎪      1/2  0  U1  U2  U3  U3xy  U4  N1  N3  S  SS  F  FF  A1  A2  A3  A4  A5  A55
   ⎪     V5  +   -   -   -   -   -    +   -   -   -  -   +  -   -   +   +   -   -
   ⎪     II  -   -   -   -   -   -    -   -   -   -  -   +  -   -   -   +   -
   ⎪
   ⎪  2. PS
   ⎪      P+  P-  WW  PWW+  PWW-  L
   ⎪      +   +   +    -     -    -
   ⎪
   ⎪  3. IR
   ⎪      D1  D2  f  M1  M3  M2  M4
86⎨      -   -   -  -   +   -   +
   ⎪
   ⎪  4. AH
   ⎪      V+  2+  V-  2-  Vn+  2n+  Vn-  2n-
   ⎪      -   -   -   -   -    -    +    -
   ⎪
   ⎪  5. CH
   ⎪      Q1  Q2
   ⎪      -   +
   ⎪
   ⎪  6. CC
   ⎪     rrr  RRR  r  R  RR  rr  rR  R+  R-  Rw+  Rw-  PT  pt  Rn    Y
   ⎩      -   +    -  -  -   -   +   -   +   +    -    -   +   -
   ─────────────────────────────────────────────────────

⎧  SUG:    A.
   ⎪
   ⎪        HR. 118
88⎨
   ⎪
   ⎪  E:\77\CARDIO\P--------C     M
   ⎩      **** ???? ***
```

FIG. 14.

METHOD OF AND ARRANGEMENT FOR DIAGNOSING BRAIN DISEASE

CROSS-REFERENCE TO RELATED APPLICATION

This application is a division of application Ser. No. 822,525, filed 17 Jan. 1992 which, in turn, is a continuation-in-part of application Ser. No. 397,695 filed 30 Oct. 1989 and now abandoned.

BACKGROUND OF INVENTION

1. Field of the Invention

This invention generally relates to a method of, and an arrangement for, determining a condition of a sample to be analyzed and, more particularly, to the early and accurate diagnosis of heart and/or brain disease in human patients.

2. Description of the Related Art

Heart and brain disease are still the leading causes of death around the world. Conventional detection of such disease relies on electrocardiograph (EKG) and electroencephalograph (EEG) devices for measuring heart and brain wave activity by sensing electrical signals at various sites on the human body, and by recording these signals as waveforms. A cardiologist or a neurologist evaluates the EKG/EEG waveforms to determine abnormalities therein. Such evaluation requires considerable training and skill. Even despite a high degree of training and skill, an EKG/EEG waveform can still be interpreted as indicating normal heart/brain activity even in the presence of advanced coronary artery disease and brain epilepsy. Experience has shown that conventional EKG/EEG devices, although useful, are not sufficiently reliable to diagnose heart/brain disease, either due to insufficient sensitivity or specificity, and certainly not at an early stage of heart/brain disease. It has been estimated that over 50% of people with occlusive coronary artery disease or brain epilepsy have been reported to have normal EKG/EEG waveforms.

The prior art has proposed several approaches to extract more information from the EKG/EEG signals. U.S. Pat. No. 4,924,875 teaches the extraction of information regarding ischemia, propensity to ventricular tachycardia and other disorders in the heart which affect cardiac electrical activity. U.S. Pat. No. 4,579,125 teaches the determination of the frequency content of EEG signals from the brain. U.S. Pat. No. 4,421,122 teaches the topographic mapping of a person's brain.

In the EKG field, such functions as the frequency content of the EKG signals, e.g. power spectrum, and the amplitude histogram, e.g. occurrence frequency, have been analyzed. In the EEG field, such functions as the power spectrum, the coherence and the cross correlation have been considered. However, in each case, usually a small portion of one cycle of the processed EKG/EEG signal has been utilized. This has proven to be an unreliable diagnostic tool.

EKG/EEG signals arise from the discharge of electrical potentials from hundreds of thousands of electrically active cells, thereby resulting in a complex resultant signal. Isolated signal processing analysis of small portions of the processed EKG/EEG signal does not produce reliable data. The analysis of a single function characteristic of the EKG/EEG signal simply does not produce sufficient or reliable information. Conventional time and frequency domain analysis of the EKG/EEG signal, as well as the analysis of isolated minor portions of single functions of the EKG/EEG signal, fail to address information regarding non-linearities as well as cross correlation, coherence and phase angle over time. The joint effect of all these functions, particularly over an extended test period of many test cycles, has not been considered. As a result, the early and reliable detection of heart and brain disease, as well as the specific diagnosis of the type of heart disease, are not presently available, particularly at a time when the chronic disease might be treated and its progress retarded or halted.

SUMMARY OF THE INVENTION

1. Objects of the Invention

It is a general object of this invention to advance the state of the diagnostic art for detecting heart and/or brain disease.

Another object of this invention is to detect heart/brain disease at an early stage in its progress.

Still another object of this invention is to non-invasively and accurately diagnose heart/brain disease.

A further object of this invention is to diagnose different types of heart disease.

2. Features of the Invention

In keeping with these objects and others, which will become apparent hereinafter, one feature of this invention relates, in its broadest aspect, to determining a condition of a sample by acquiring electrical analog signals from the sample. In one preferred embodiment, the signals are EKG signals obtained from a surface of the body of a patient by placement of a plurality of surface electrodes at various sites thereon. In another preferred embodiment, the signals are EEG signals obtained from a surface of the head of the patient, also by placement of a plurality of surface electrodes at various sites thereon.

The method and arrangement of this invention, however, are not intended to be limited to the determination of heart disease from EKG signals, or of brain disease from EEG signals. This invention can be extended to the analysis of any biological signals generated during the course of such medical examinations as an electromyogram, electrobasogram, electrocorticogram, electrocystogram, electrogastrogram, electrometrogram, electronystagmogram, electro-oculogram, electroretinogram, electrospinogram, etc. In addition, the method and arrangement of this invention can be extended to the analysis of non-biological signals, e.g. physical signals or chemical signals, obtained during the course of measurement in a seismogram, eletrophoretogram, thermogram, etc.

This invention processes the analog signals, whether biological or not, and mathematically determines a plurality of functions descriptive of the sample being analyzed. Thus, in the case of EKG signals, the functions include, as described in detail below, the power spectrum characteristic, the coherence characteristic, the phase angle characteristic, the impulse response characteristic, the cross correlation characteristic and the amplitude histogram characteristic. Each of these functions carries a wealth of different information about the EKG signals, particularly when the functions are processed over an extended time period which, in the preferred embodiment, is 15 cycles lasting 10 seconds per cycle. The extended time period is many orders of magnitude greater than the typical analysis of EKG signals which, at best, process a minor fraction of one heart cycle of a heart function characteristic.

In accordance with this invention, a set of indices is established for each function. Each index has two states. The positive state indicates an abnormal condition for the sample. A negative state indicates a normal condition. The indices generally relate to the pattern or shape of the waveform of each function characteristic. As described in detail below, the preset indices include the magnitude of peaks, the intervals between peaks, the curvature of the peaks, the number of bends, etc.

An integrated index pattern of the states of the indices derived from a plurality, if not all, of the functions is generated. This integrated pattern is then matched against a stored collection of index patterns whose condition (i.e., diagnosis) is known. The best match then determines the diagnosis for the patient being analyzed.

The collection of stored index patterns is based on storing the index patterns of a multitude, e.g., many thousands, of patients whose condition is known and whose condition was confirmed by medical examination and testing. Thus, patients having myocarditis, for example, have index patterns which, when grouped together, have a distinctive pattern. Patients having a different heart disease have differently distinctive index patterns. As previously mentioned, the index pattern of the patient being tested is compared to each group of known patterns to find the best match and, hence, the diagnosis.

In the case of a cardiac patient, the collection of stored index patterns are advantageously grouped into the following eight categories: coronary heart disease, rheumatic heart disease, pulmonary heart disease, congenital heart disease, myocarditis, myocardiopathy, fibrillation and ventricle hypertrophy. This invention thus can match the cardiac patient's measured pattern against the patterns of these categories to select the one that best describes the patient's cardiac condition.

Hence, rather than relying on data extracted over a limited time for a single function, this invention relies on data extracted over an extended time from a plurality of functions, some of which have not heretofore been used in the diagnosis of heart/brain disease.

The novel features which are considered as characteristic of the invention are set forth in particular in the appended claims. The invention itself, however, both as to its construction and its method of operation, together with additional objects and advantages thereof, best will be understood from the following description of specific embodiments.

BRIEF DESCRIPTION OF THE DRAWINGS

FIG. 14 is a sample print-out of a cardiogram analysis for the patient under test;

DETAILED DESCRIPTION OF THE PREFERRED EMBODIMENTS

Figure 1:
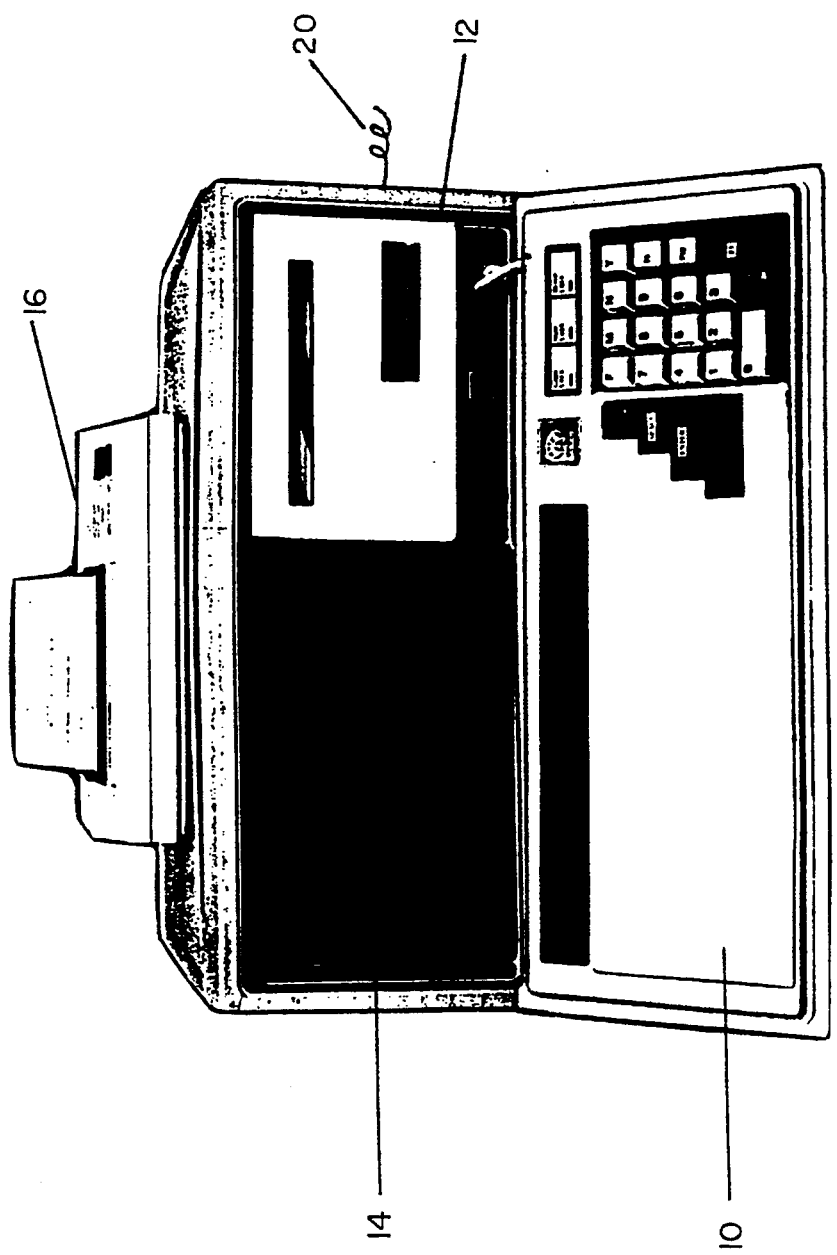
FIG. 1 is a front view of an arrangement in accordance with the method of this invention.

Referring now to the drawings, reference numeral 10 generally identifies an arrangement for diagnosing heart/brain disease in accordance with the method of this invention. Arrangement 10 includes a keyboard 12 for manual data entry and operational control, a monitor 14 for displaying and plotting data and a printer 16 for printing a written data record. As described below, electronic circuitry within the arrangement is employed to process EKG or EEG signals in order to obtain a diagnosis of a condition of a patient 18.

Figure 3:
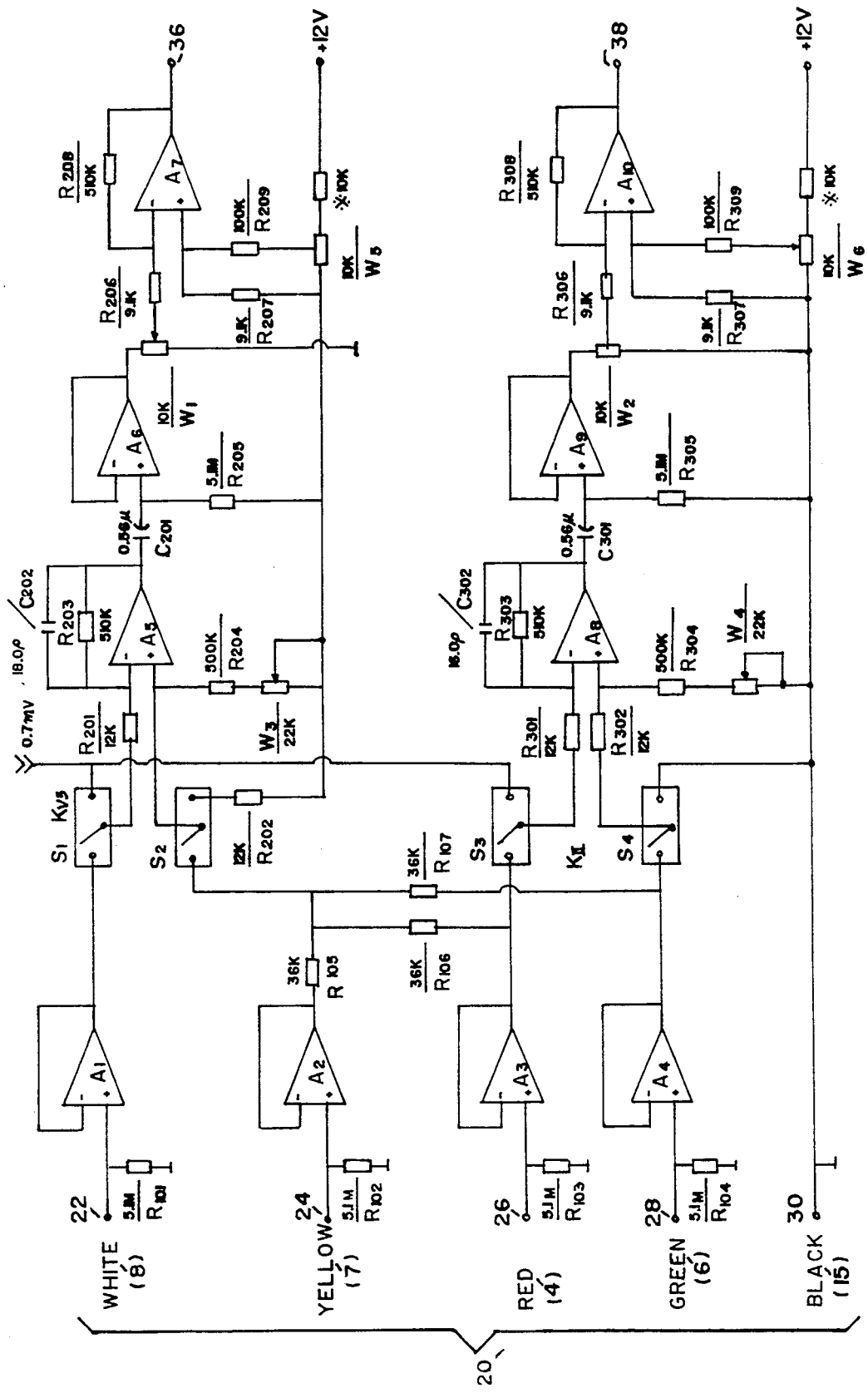
FIG. 3 is an electrical schematic diagram of the EKG combiner network depicted in FIG. 2.

In the case of diagnosing heart disease, the arrangement 10 is connected to the patient by a cable set 20 in a conventional EKG hook-up. The cable set 20 includes five wires each having a surface electrode positioned at various fixed sites on the patient's body. As depicted in FIG. 3, an electrode 22 connected to a conventional EKG "white" wire is placed over the area of the patient's body overlying the left ventricle. An electrode 24 connected to a conventional EKG "yellow" wire is placed over the left hand. An electrode 26 connected to a conventional EKG "red" wire is placed over the right hand. An electrode 28 connected to a conventional EKG "green" wire is placed over the left leg. An electrode 30 connected to a conventional EKG "black" wire is placed over the right leg.

Figure 2:
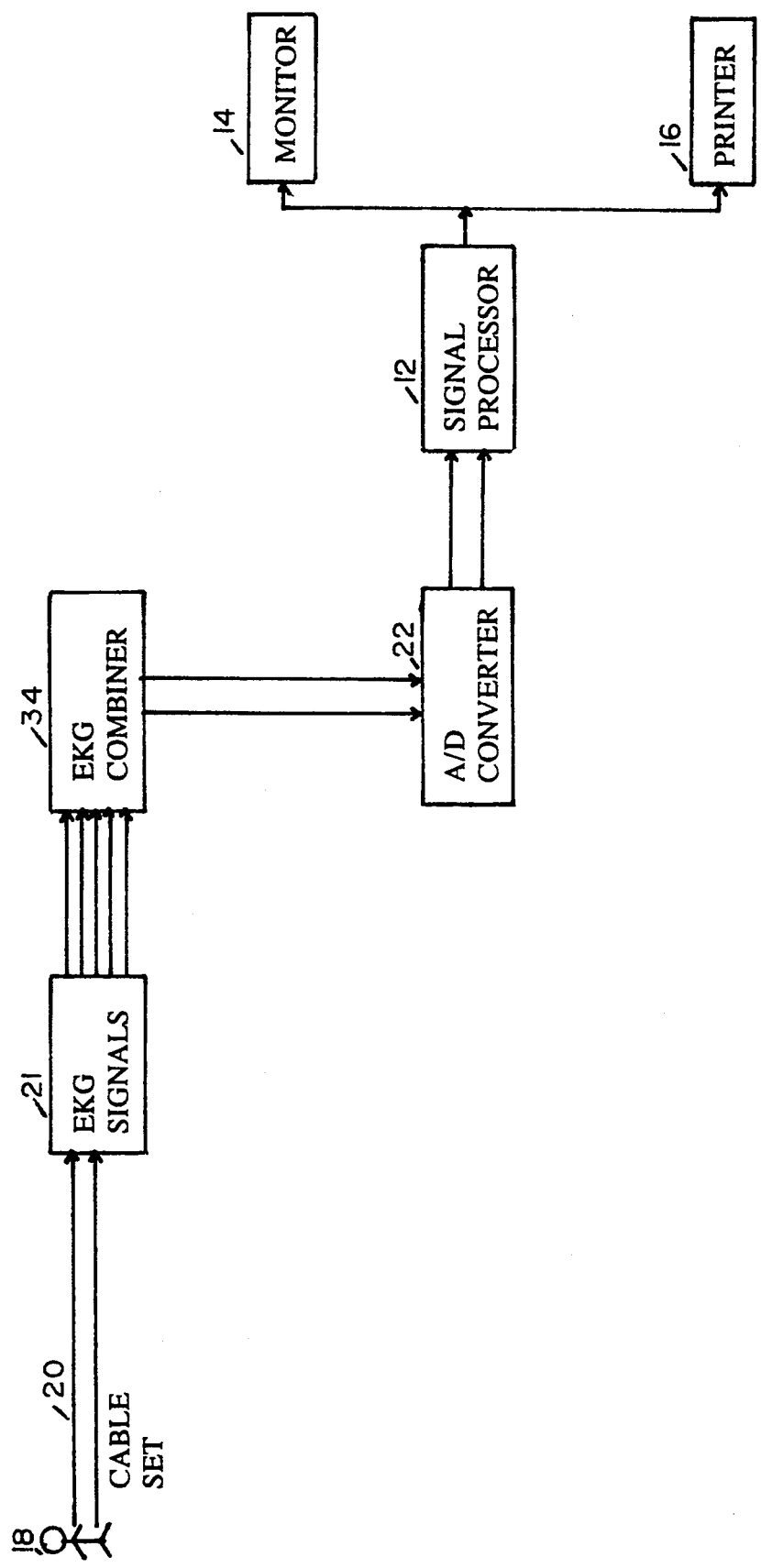
FIG. 2 is a block diagram of the arrangement of FIG. 1 connected to a patient.
Figure 5:
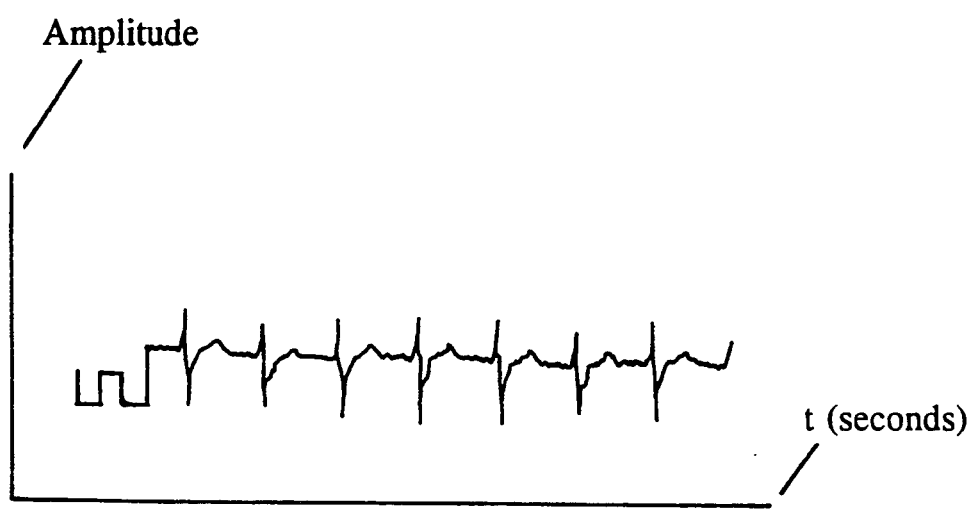
FIG. 5 is an EKG waveform from the left ventricular lead of a patient under test.

These electrodes 22–30 generate time-dependent electrical analog signals, as represented by block 32 in FIG. 2. These signals are fed into and combined in a novel manner in combiner network 34 which is shown in detail in FIG. 3. The combiner network 34 combines the afore-mentioned five EKG signals into a pair of output signals at outputs 36, 38. The output signal at output 36 is conventionally designated hereinafter as "lead V5" and is indicative of the activity of the left ventricle. This analog signal is shown in FIG. 5 wherein amplitude is plotted against time. The FIG. 5 graph shows left ventricular activity for ten seconds. The output signal at output 38 is conventionally designated hereinafter as "lead II" and is indicative of the activity of a broad area of the heart. The various input signals from electrodes 22–30 are amplified in differential amplifiers A1–A4, and switched by switching circuits S1–S4, before being again amplified and conducted along two independent paths, one path being comprised of differential amplifiers A5–A7, and the other path being comprised of differential amplifiers A8–A10.

As best shown in FIG. 2, the output analog EKG signals at outputs 36, 38 are sampled and digitized in an analog-to-digital converter 40. The digital signals are processed by a programmed microcomputer or signal processor 42. The results of the signal processing, as described below, are displayed on monitor 14 or printed by printer 16.

Figure 4:
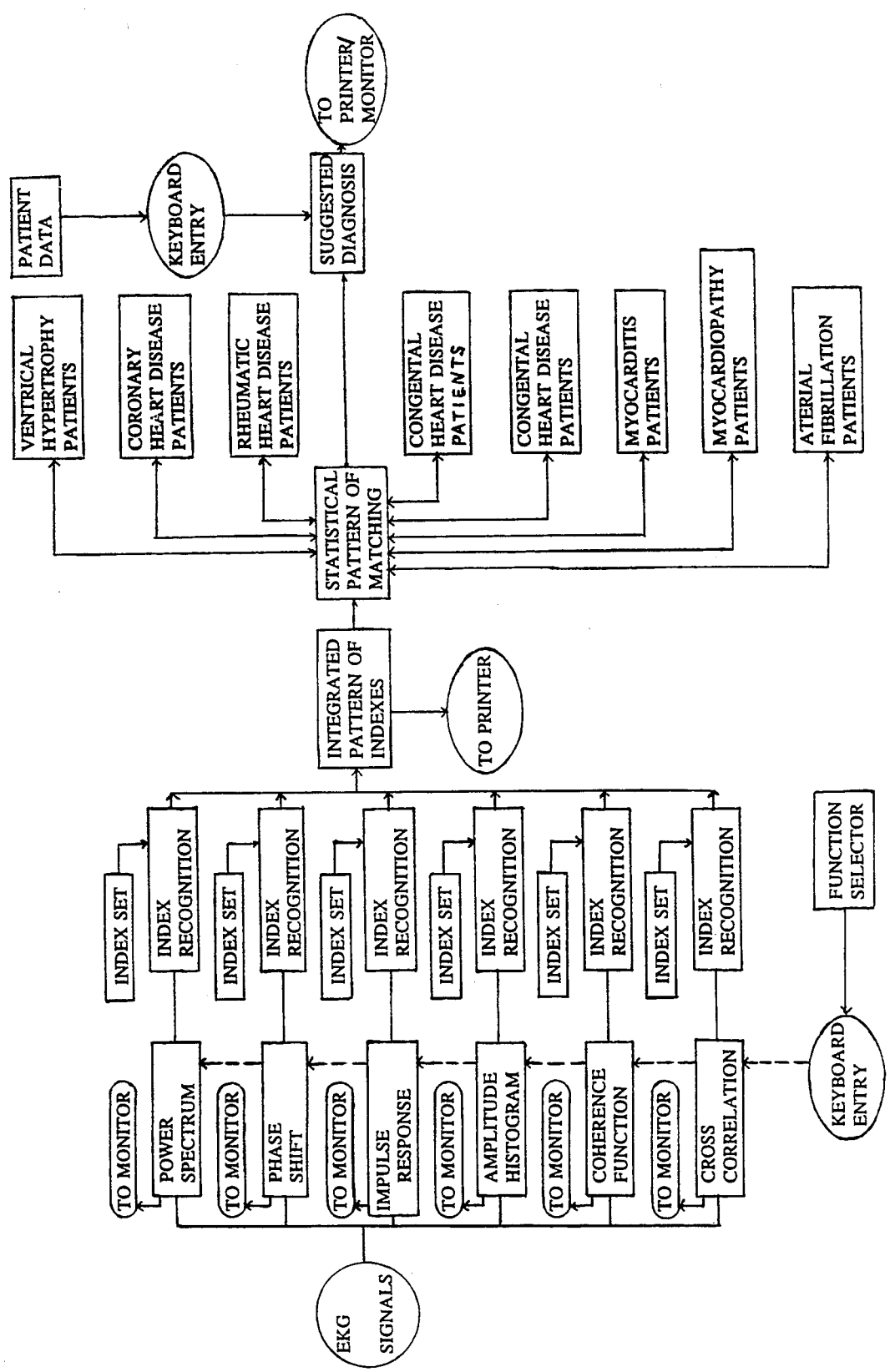
FIG. 4 is an overall block diagram of the signal processor depicted in FIG. 2.

An overview of the signal processing is depicted in FIG. 4. The digital EKG signals from outputs 36, 38 are fed to function blocks 44, 46, 48, 50, 52 and 54 wherein the power spectrum, phase angle, impulse response, amplitude histogram, coherence and cross-correlation are respectively mathematically determined. In a preferred embodiment, all of these functions are determined and used in making the diagnosis. However, it is sufficient if at least two of these functions are determined. The choice of function to be determined at any particular time is selected by a function selector 56 which advantageously is a function key on the keyboard 12. Once mathematically determined, any particular function can be displayed as an analog waveform on the monitor 14.

Figure 6:
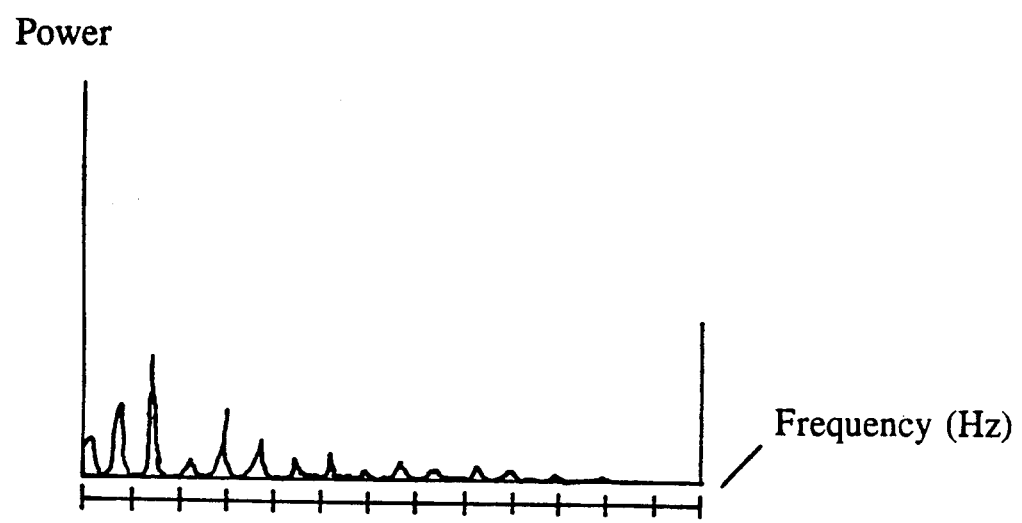
FIG. 6 is a graph of the power spectrum characteristic of the waveform of FIG. 5.

The power spectrum function 44 is calculated as follows: The auto power spectrum $G_{xx}(f)$ for lead V5 is determined from equation (1):

$$G_{xx}(f) = S_x(f) \cdot S_x(f)^* \tag{1}$$

where $S_x(f)$ is the Fourier transform of the time-dependent, lead V5 signal $f_x(t)$ depicted in FIG. 5, and where $S_x(f)^*$ is the complex conjugate. The power spectrum $G_{xx}(f)$ for a patient under test is depicted in FIG. 6 wherein power is plotted against frequency.

Figure 7:
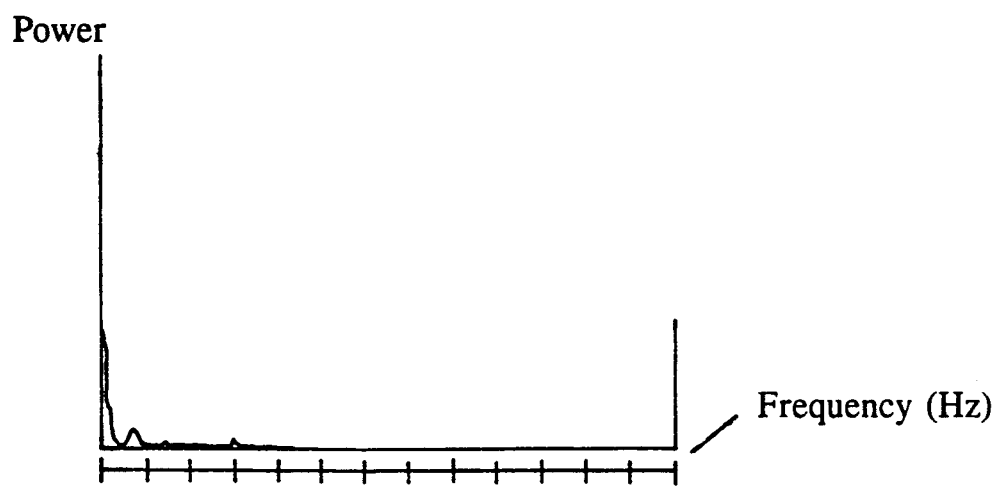
FIG. 7 is a graph analogous to FIG. 6 but of the EKG waveform from the whole heart lead.

The auto power spectrum $G_{yy}(f)$ for lead II is determined from equation (2):

$$G_{yy}(f) = S_y(f) \cdot S_y(f)^* \tag{2}$$

where $S_y(f)$ is the Fourier transform of the time-dependent, lead II signal $f_y(t)$, and where $S_y(f)^*$ is the complex conjugate. The power spectrum $G_{yy}(f)$ for a patient under test is depicted in FIG. 7 wherein power is plotted against frequency.

The phase angle function 46 is calculated as follows: First, the amplitude ratio of the transfer function $H_{xy}(f)$ is determined from equation (3):

$$H_{xy}(f) = G_{xy}(f)/G_{xx}(f)^* \tag{3}$$

where the cross power spectrum $$G_{xy}(f) = S_x(f) \cdot S_y(f)^* \tag{4}$$

and where $G_{xx}(f)$ is obtained in equation (1).

Second, the phase angle $\theta_{xy}(f)$ of the transfer function $H_{xy}(f)$ is determined from equation (5):

$$\theta_{xy}(f) = \tan^{-1}\{[IM(H_{xy}(f))]/[RE(H_{xy}(f))]\} \tag{5}$$

where IM and RE are the real and imaginary parts of the transfer function.

Figure 8:
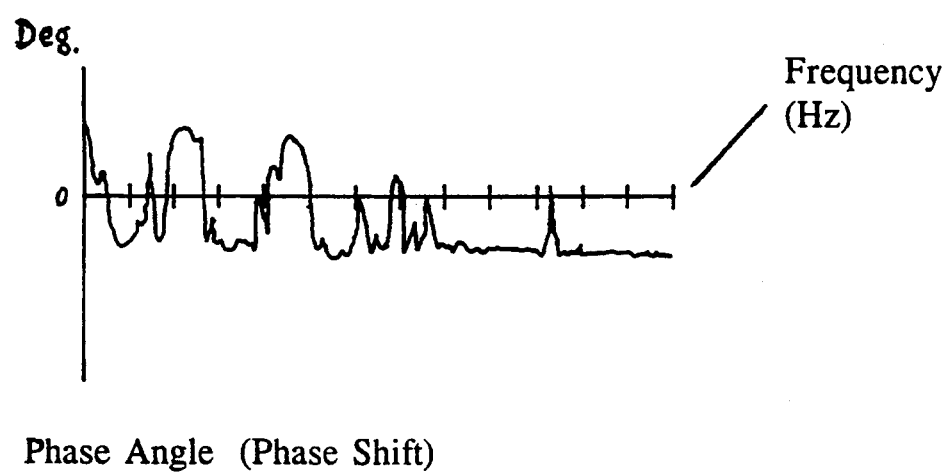
FIG. 8 is a graph of the phase angle characteristic of the patient under test.

The phase angle is a measure of the time difference between the left ventricular and whole heart signals and is depicted in FIG. 8 wherein phase in degrees is plotted against frequency. Phase leads and lags are respectively indicated above and below the reference line.

The impulse response function 48 is calculated as follows: The impulse response $IH_x(f)$ is determined from equation (6):

$$IH_x(f) = F^{-1}H_{xy}(f) \tag{6}$$

where $F^{-1}$ is the inverse Fourier transform of the transfer function $H_{xy}(f)$ defined in equation (3).

Figure 9:
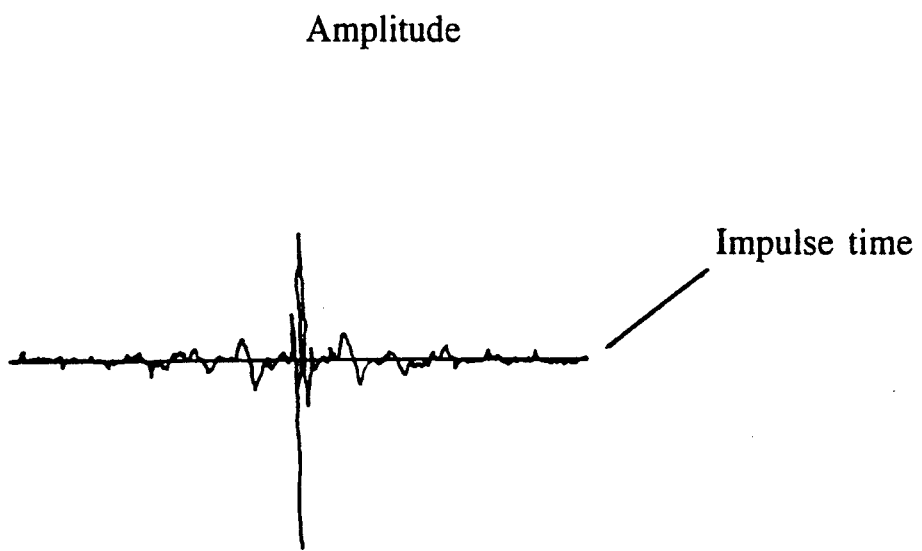
FIG. 9 is a graph of the impulse response characteristic of the patient under test.

The impulse response is a measure of the output response of the heart solely in response to the input of the left ventricular signal and is depicted in FIG. 9 wherein amplitude is plotted against impulse.

Figure 10:
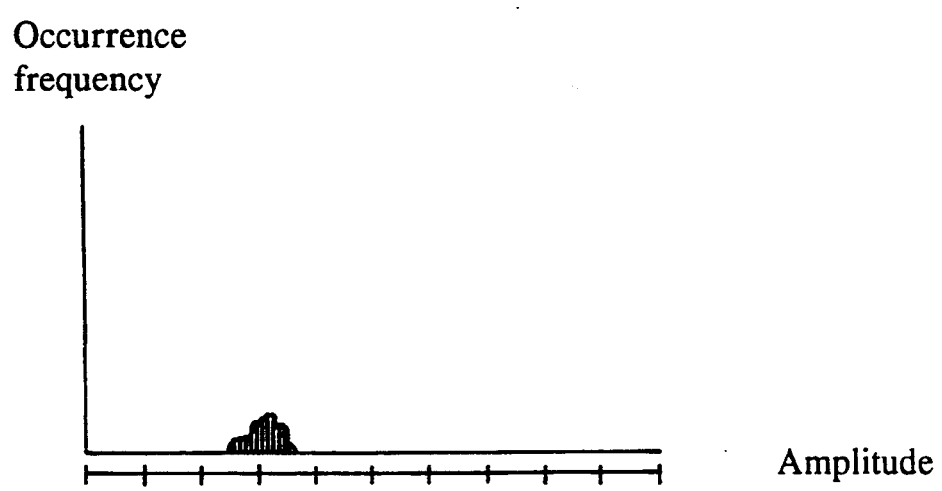
FIG. 10 is a graph of the amplitude histogram characteristic from the left ventricular lead of the patient under test.
Figure 11:
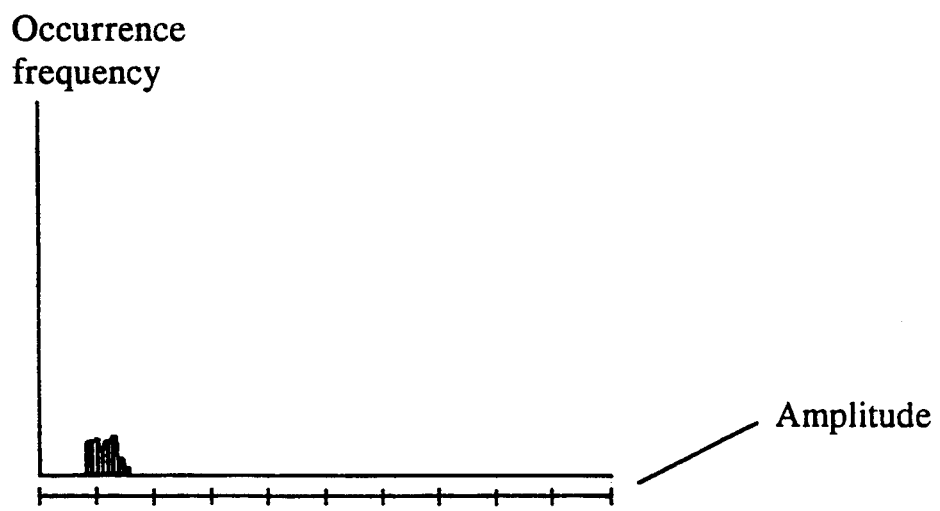
FIG. 11 is a graph analogous to FIG. 10 but from the whole heart lead.

The amplitude histogram function 50 is a standard statistical analysis of the amplitudes present in the left ventricular and whole heart signals and are respectively depicted in FIGS. 10 and 11 wherein the occurrence frequency is plotted against specific amplitudes. These plots indicate how many times a given amplitude is present in the left ventricular and whole heart signals.

Figure 12:
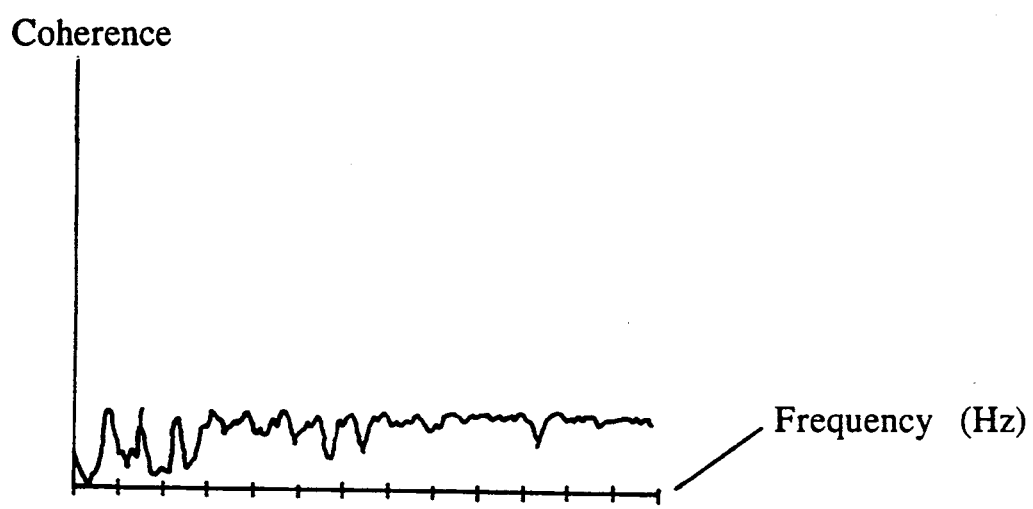
FIG. 12 is a graph of the coherence characteristic of the patient under test.

The coherence function 52 is calculated as follows: The coherence $\gamma_{xy}(f)$ is determined from equation (7):

$$\gamma_{xy}(f) = G_{xy}(f)/G_{xx}(f) \cdot G_{yy}(f) \tag{7}$$

where $G_{xy}(f)$, $G_{xx}(f)$ and $G_{yy}(f)$ are defined in equations (4), (1) and (2). The coherence is depicted in FIG. 12 wherein coherence is plotted against frequency.

Figure 13:
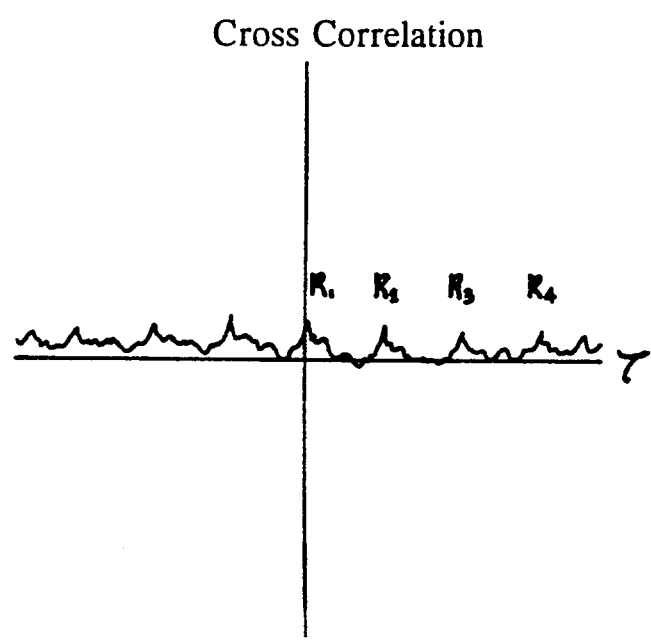
FIG. 13 is a graph of the cross correlation characteristic of the patient under test.

The cross correlation function 54 is calculated as follows: The cross correlation $\phi_{xy}(\tau)$ is determined from equation (8):

$$\phi_{xy}(\tau) = \lim_{t \to \infty} \frac{1}{T} \int_0^\infty f_x(t) \cdot f_y(t + \tau)\, dt \tag{8}$$

where $f_x(t)$ and $f_y(t)$ are the left ventricular and whole heart signals, where $\tau$ is the delay time between the signals, and where T is the test period, typically 150 seconds. The cross correlation is a measure of the correspondence of the signals and is depicted in FIG. 13 wherein cross correlation is plotted against the delay time.

Returning to FIG. 4, after the functions 44–54 have been calculated, they may be sequentially displayed on the monitor for evaluation by a technician, or, preferably, the function waveforms, as depicted in FIGS. 6–12, are stored in a random access memory and subjected to a battery of tests in which the presence or absence of various indices are recognized. These indices all relate to the overall shape of the various function waveforms and are established in advance. Each function has its own individual pre-set indices as represented by blocks 58–88 in FIG. 4. Each of these indices has two states. A positive state indicates an abnormal condition. A negative state indicates a normal condition. The recognition of the indices occurs in a pattern recognition program as represented by blocks 70–80. The pre-set indices are set forth below for each function for an EKG analysis:

(I) Power Spectrum (1) ½—Is the amplitude ratio of the first peak/second peak above a limit?

(2) O—Is shape of any of first four peaks rounded similar to omega (Ω)?

(3) U1—Do any of first four peaks have a twinned peak?

(4) U2—Are the intervals between any of first four peaks unequal?

(5) U3—Is the inequality of the intervals between any of the first four peaks above a limit?

(6) U3xy—Same as U3 but are any two peaks simultaneously positive?

(7) U4—Is the shape of any peak similar to a hill (∫\)?

(8) U5—Is the shape of any peak similar to a mountain (∫h)?

(9) N1—Is the first peak null?

(10) N3—Is the third and/or fourth peak null?

(11) S—Is the heart rate below 60 beats per minute?

(12) SS—Is the heart rate below 50 beats per minute?

(13) F—Is the heart rate over 100 beats per minute?

(14) FF—Is the heart rate above 120 beats per minute?

(15) A1—Is the amplitude of the first peak above a limit?

(16) A2—Is the amplitude of any two of the first four peaks above a limit?

(17) A3—Is the amplitude of the second peak above a limit?

(18) A4—Is the amplitude of the third and/or fourth peak above a limit?

(19) A5—Is any one of the 5th–12th peaks higher than the first peak?

(20) A55—Are any two of the 5th–12th peaks higher than the first peak?

(21) A6—Are more than two of the 5th–12th peaks higher than the first peak?

(22) Nn—Are the first and second peaks higher than the third and fourth peaks?

(23) nN—Are the third and fourth peaks higher than the first and second peaks?

(24) Nnn—Is the first peak higher than the second, third and fourth peaks?

(25) nnN—Is the first peak lower than the second, third and fourth peaks?

(II) Phase Angle

(26) P+—Does the phase angle lag above a limit at various frequency bands?

(27) P—Does the phase angle lead above a limit at various frequency bands?

(28) WW—Is the shape of the waveform similar to the letter "W" at various frequency bands?

(29) PW+—Do indices 26 and 28 co-exist at various frequency bands?

(30) PW—Do indices 27 and 28 co-exist at various frequency bands?

(31) L—Is the phase angle too small plus is the impulse response too even?

(32) U—Does the waveform have the shape of the letter "U" at various frequency bands?

(33) W—Are there two or more U-shaped waves?

(34) V—Does the wave form have a long upward slope?

(35) Y—Is the slope of the waveform positive or negative?

(36) X—Do indices 32 and 35 or 32 and 33, co-exist?

(37) Z—Does the waveform have waves shaped like the letter "Z"?

(III) Impulse response

(38) D1—Does the waveform have a double top plane wave resembling Z or ⊓⊔ ?

(39) D2—Does the waveform have a stair steps wave resembling  ?

(40) f—Is the main response impulse negative?

(41) M1—Does the main response impulse have a twin peak?

(42) M2—Does the shape of the main response impulse resemble the letter "M"?

(43) M3—Does the main response impulse have more than three peaks?

(44) M4—Does the main response impulse have a peak that is too wide?

(45) M5—Does the side response have a peak whose amplitude is above a limit?

(46) M6—Is the main response impulse totally downward?

(IV) Coherence

(47) Q1—Is the coherence of the first peak of the power spectrum below a limit?

(48) Q2—Is the coherence of the highest peak of the transfer function below a limit?

(V) Amplitude Histogram

(49) V+—Is the amplitude of lead V5 above a limit?

(50) 2+—Is the amplitude of lead II above a limit?

(51) V—Is the amplitude of lead V5 below a limit?

(52) 2—Is the amplitude of lead II below a limit?

(53) Vn+—Is the number of bundles of the column in the amplitude histogram of lead V5 above a limit?

(54) Vn—Is the number of bundles of the column in the amplitude histogram of lead V5 below a limit?

(55) 2n+—Is the number of bundles of the column in the amplitude histogram of lead II above a limit?

(56) 2n—Is the number of bundkes of the column in the amplitude histogram of lead II below a limit?

(VI) Cross Correlation

(57) RRR—Is the amplitude of the main peak above a limit?

(58) rrr—Is the amplitude of the main peak below a limit?

(59) R—Is the main peak within a higher zone?

(60) r—Is the main peak within a lower zone?

(61) RR—Is the interval betwee R1 and R2 above a limit?

(62) rr—Is the interval between R1 and R2 too short?

(63) rR—Is the peak R1 lower than the peak R2?

(64) R2—Is the peak R2 below a limit?

(65) R+—Does the peak R1 shift to the right side?

(66) R—Does the peak R2 shift to the left side?

(67) Rw+—Is the bottom of the first positive peak below the bottom of the first negative peak, and so on for successive peaks?

(68) Rw—Is the bottom of the first positive peak above the bottom of the first negative peak, and so on for successive peaks?

(69) pt—Is the number of peaks whose amplitude is above a threshold between peaks R1 and R2 above a limit?

(70) PT—Is there one or more peaks between peaks R1 and R2 higher than peak R2 above a limit?

(71) Rn—Does R2 have a twin peak or a zigzag shape?

(72) Rm—Is the peak R1 too wide?

(73) Rv—Is one bend of R1 too steep in slope?

Once the state of each index has been recognized, an integrated pattern 82 is generated. The integrated pattern contains the states of the indices from at least two, if not all, the above functions. The integrated pattern 82 can be printed out by the printer as set forth in the sample cardiogram analysis printout depicted in FIG. 14.

The printout is subdivided into three parts. A first part 84 contains patient data 90 entered via the keyboard 12. A second part 86 contains the aforementioned six functions together with the individual index legends and the results (+) or (−) of the index recognition. Some of the indices as set forth above have been deleted from FIG. 14 for ease of illustration. A third part 88 sets forth the diagnosis which is produced as described below.

Once the integrated pattern 82 is generated, it is fed into a statistical pattern matching program 92 to which a massive data bank is connected. The data bank includes a multitude of index patterns taken from thousands of patients whose heart condition is known, usually by direct medical examination. The index patterns of different diseases have different index sequences. Once the best match between the measured integrated pattern 82 and one of the stored patterns is obtained, a diagnosis 110 is made.

Advantageously, in the case of cardiac analysis, the data bank is separated into eight distinctive categories, namely, ventricle hypertrophy disease 94, coronary heart disease 96, rheumatic heart disease 98, pulmonary heart disease 100, congenital heart disease 102, myocarditis 104, myocardiopathy 106, and fibrillation 108. This invention can thus distinguish between these different types of heart diseases.

Figure 15:
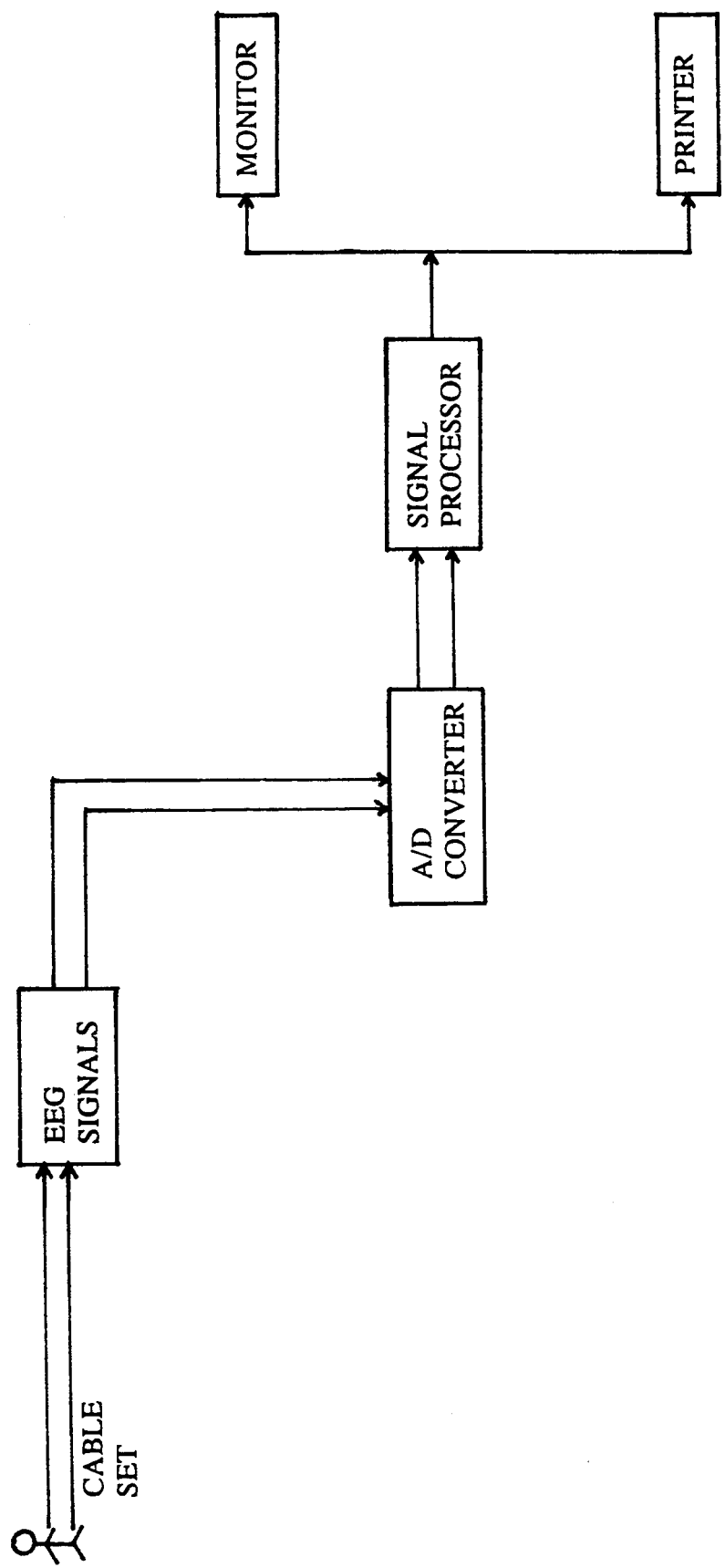
FIG. 15 is a view analogous to FIG. 2, but foe an EEG hook-up.
Figure 17:
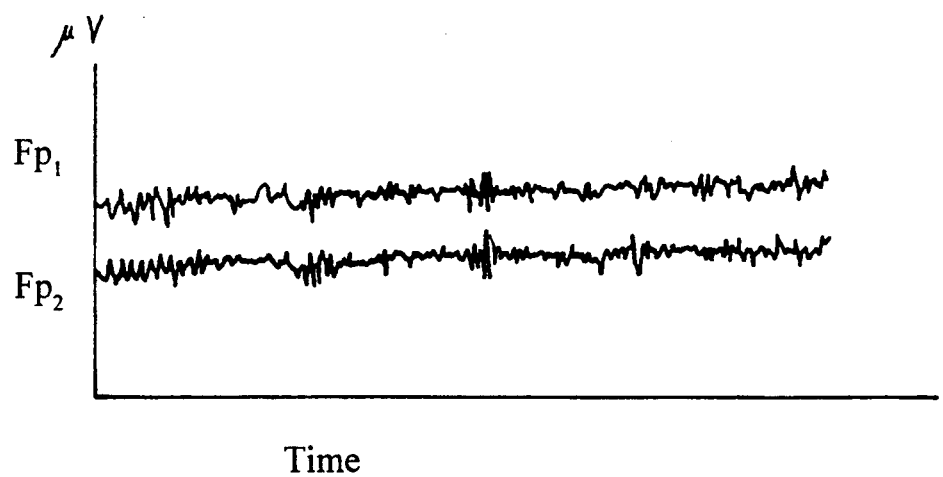
FIG. 17 is a graph of an EEG signal wherein amplitude is plotted against time.

In a completely analogous manner, the arrangement 10 can be used to diagnose brain disease. As depicted in FIG. 15, the hook-up to the patient 18 is different. Instead of using a five-cable set, a two-wire cable set 112 is employed. Each wire has a surface electrode placed at the left and right frontal areas of the brain on the skull of the patient. These are conventionally designated as the "$F_{p1}$ and $F_{p2}$ leads". A representative $F_{p1}$ or $F_{p2}$ signal is shown in FIG. 17 wherein amplitude is plotted against time.

As before, the electrodes produce two analog electrical EEG signals, as represented by block 114, which are fed directly into the analog-to-digital converter 40. The signals are sampled and digitized within the converter. The digital EEG signals are then conducted to the signal processor 42 whereupon, after processing, the data may be displayed on the monitor 14 or printed by the printer 116.

Figure 16:
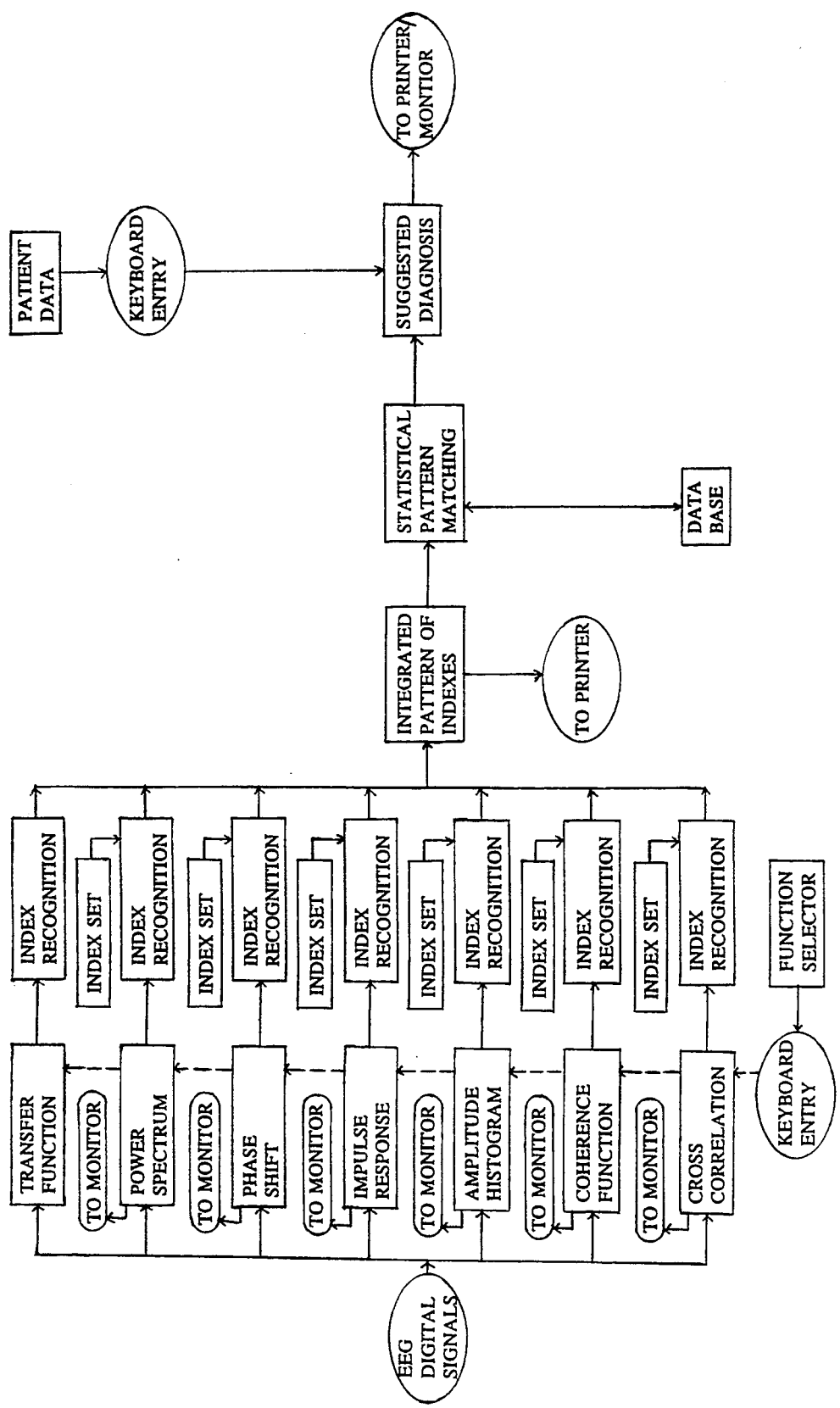
FIG. 16 is a view analogous to FIG. 4, but of an EEG test.
Figure 18:
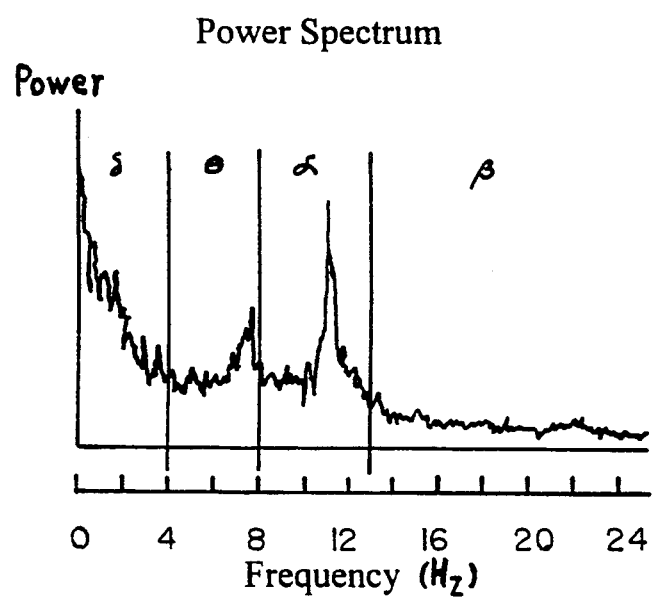
FIG. 18 is a graph of the power spectrum characteristic for the EEG signal of FIG. 17.

The overall EEG signal processing is depicted in FIG. 16. Transfer function 43 rather than phase angle 46 is determined, Otherwise, the various functions 43-54 are determined as before. For example, a representative power spectrum characteristic is depicted in FIG. 18 wherein power is plotted against frequency. As also shown in FIG. 18, the delta ($\delta$), theta ($\theta$), alpha ($\alpha$), and beta ($\beta$) frequency bands are indicated. In addition, the aforementioned transfer function 43 is mathematically determined. The essential difference is that pre-set indices 115-126 and index recognition programs 127-138 are different. For example, the pre-set indices for each function are:

(1) HW—Is the highest peak of the power spectrum in the delta band above a limit as well as too wide?

(2) OH—Is the highest peak of the power spectrum in the theta band above a limit?

(3) As- -—Is the main peak of the power spectrum of the alpha wave shifted to the theta band?

(4) As+—Is the main peak of the power spectrum of the alpha wave shifted to the beta band?

(5) EV—Is the transfer function curve too even in the low frequency range?

(6) RC—Is the highest peak of the coherence in the theta band higher than that in the alpha band?

(7) RT—Is the highest peak of the transfer function in the theta band higher than that in the alpha band?

(8) PA—Does the shape of the phase angle wave resemble the letter "W"?

(9) LF—Is there a late fluctuation of the impulse response?

(10) L3—Is there a delay of the third peak of the impulse response?

(11) F/A—Is the ratio of the occurrence frequency/amplitude of the amplitude histogram above a limit?

As before, once the states of the various indices are recognized, an integrated pattern 140 is generated and statistically matched in a matching program 142 to which a massive data bank 144 of known brain disease patterns is connected. A suggested brain disease diagnosis 146 is then generated.

As previously mentioned, the test procedure lasts for an extended time period of multiple heart and brain wave cycles. In the case of a cardiac patient, fifteen sets of data are collected, each over a ten second time interval. The resultant 150-second time period has been found to be sufficient from which to extract reliable data.

It will be understood that each of the elements described above, or two or more together, also may find a useful application in other types of constructions differing from the types described above.

While the invention has been illustrated and described as embodied in a method of and arrangement for diagnosing heart and brain disease, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

I claim:

1. A method of diagnosing a brain condition of a patient, comprising the steps of:
    (a) acquiring electrocardiographic signals from the patient;
    (b) mathematically determining a plurality of functions descriptive of the patient from the electroencephalographic signals;
    (c) establishing a set of indices for each function, each index having two states, each indicative of the brain condition of the patient;
    (d) recognizing the state of each index for each function;
    (e) generating an integrated pattern of the states of the indices from a plurality of the functions;
    (f) storing a collection of index patterns, each containing a multitude of patterns of the states of indices for a multitude of patients whose brain condition is known; and
    (g) matching the generated integrated pattern against the stored collection of index patterns to determine the brain condition of the patient being diagnosed.

2. The method according to claim 1, wherein the acquiring step is performed by acquiring the electroencephalographic signals as a function of time from a surface of the skull of the patient being diagnosed through a plurality of skull surface eletroencephalo electrodes over a multicycle test period.

3. The method according to claim 2, wherein the acquiring step is performed by processing the electroencephalographic signals into analog signals that are indicative of the brain activity at the right and left frontal areas of the brain.

4. The method according to claim 2, wherein the mathematically determining step is performed by converting the electroencephalographic time-dependent signals into respective power spectrum characteristics wherein power is a function of frequency.

5. The method according to claim 4, wherein the establishing step is performed by setting in advance pre-set parameters, including location, amplitude and width of highest peak; and wherein the recognizing step is performed by comparing each power spectrum characteristic against the pre-set parameters, and by determining the state of each index for each power spectrum characteristic in response to the comparing step.

6. The method according to claim 2, wherein the mathematically determining step is performed by converting the electroencephalographic time-dependent signals into an amplitude ratio of a transfer function characteristic wherein transfer function is a function of frequency.

7. The method according to claim 6, wherein the establishing step is performed by setting in advance pre-set parameters, including amplitude differences between peaks, and amplitude of the characteristic within a range; and wherein the recognizing step is performed by comparing the transfer function characteristic against the pre-set parameters, and by determining the state of each index for the transfer function characteristic in response to the comparing step.

8. The method according to claim 7, wherein the mathematically determining step is performed by converting the electroencephalographic time-dependent signals into a coherence characteristic wherein coherence between the electroencephalographic signals is a function of frequency.

9. The method according to claim 8, wherein the establishing step is performed by setting in advance pre-set parameters, including amplitude of individual peaks within a range; and wherein the recognizing step is performed by comparing the coherence characteristic against the pre-set parameters, and by determining the state of each index for the coherence characteristic in response to the comparing step.

10. The method according to claim 2, wherein the mathematically determining step is performed by converting the electroencephalographic time-dependent signals into an impulse response characteristic wherein amplitude is a function of impulse time.

11. The method according to claim 10, wherein the establishing step is performed by setting in advance pre-set parameters, including the times of peaks and valleys in the characteristic, amplitude differences of the peaks and valleys, and the amplitude and shape of the main peak; and wherein the recognizing step is performed by comparing the impulse response characteristic against the pre-set parameters, and by determining the state of each index for the impulse response characteristic in response to the comparing step.

12. The method according to claim 2, wherein the mathematically determining step is performed by converting the electroencephalographic time-dependent signals into amplitude histogram characteristics wherein occurrence frequency is a function of amplitude.

13. The method according to claim 12, wherein the establishing step is performed by setting in advance pre-set parameters, including the ratio between the occurrence frequency and the maximum amplitude of each characteristic; and wherein the recognizing step is performed by comparing each amplitude histogram characteristic against the pre-set parameters, and by determining the state of each index for each amplitude histogram characteristic in response to the comparing step.

14. The method according to claim 11, wherein the generating step is performed by generating the integrated pattern from all of said functions.

15. A method of diagnosing a brain condition of a patient, comprising the steps
  (a) acquiring electrical analog electroencephalographic signals from the patient;
  (b) mathematically determining a plurality of functions descriptive of the sample from the analog signals, including power spectrum, transfer function, impulse response, cross correlation and coherence;
  (c) establishing a set of indices fof each function, each index having two states, each indicative of the condition of the patient;
  (d) recognizing the state of each index for each function;
  (e) generating an integrated pattern of the states of the indices from a plurality of the functions;
  (f) storing a collection of index patterns, each containing a multitude of patterns of the states of indices for a multitude of patients whose condition is known;
  (g) matching the generated integrated pattern against the stored collection of index patterns to determine the brain condition of the patient; and
  (h) said establishing step including:
    (1) HW—Is the highest peak of the power spectrum in the delta band above a limit as well as too wide?
    (2) OH—Is the highest peak of the power spectrum in the theta band above a limit?
    (3) As——Is the main peak of the power spectrum of the alpha wave shifted to the theta band?
    (4) As+—Is the main peak of the power spectrum of the alpha wave shifted to the beta band?
    (5) EV—Is the transfer function curve too even in the low frequency range?
    (6) RC—Is the highest peak of the coherence in the theta band higher than that in the alpha band?
    (7) RT—Is the highest peak of the transfer function in the theta band higher than that in the alpha band?
    (8) PA—Does the shape of the phase angle wave resemble the letter "W"?
    (9) LF—Is there a late fluctuation of the impulse response?
    (10) L3—Is there a delay of the third peak of the impulse response?
    (11) F/A—Is the ratio of the occurrence frequency/amplitude of the amplitude histogram above a limit?

16. An arrangement for diagnosing a brain condition of a patient, comprising:
  (a) means for acquiring electroencephalographic signals from the patient;

(b) means for mathematically determining a plurality of functions descriptive of the patient from the electroencephalographic signals;

(c) means for establishing a set of indices for each function, each index having two states, each indicative of the brain condition of the patient;

(d) means for recognizing the state of each index for each function;

(e) means for generating an integrated pattern of the states of the indices from a plurality of the functions;

(f) means for storing a collection of index patterns, each containing a multitude of patterns of the states of indices for a multitude of patients whose brain condition is known; and (g) means for matching the generated integrated pattern against the stored collection of index patterns to determin the brain condition of the patient being diagnosed.

* * * * *